(12) United States Patent
Häupl et al.

(10) Patent No.: US 7,410,151 B2
(45) Date of Patent: Aug. 12, 2008

(54) WEIGHT COMPENSATION DEVICE

(75) Inventors: Rainer Häupl, Krummennaab (DE);
Thomas Will, Kemnath (DE)

(73) Assignee: Siemens Aktiengesellschaft, Munich (DE)

( * ) Notice: Subject to any disclaimer, the term of this patent is extended or adjusted under 35 U.S.C. 154(b) by 1285 days.

(21) Appl. No.: 10/641,309

(22) Filed: Aug. 14, 2003

(65) Prior Publication Data
US 2004/0033870 A1 Feb. 19, 2004

(30) Foreign Application Priority Data
Aug. 19, 2002 (DE) ............... 102 37 873

(51) Int. Cl.
*B66D 1/14* (2006.01)
(52) U.S. Cl. .................. 254/364; 242/375.1
(58) Field of Classification Search ............ 254/278, 254/334, 364; 242/375, 375.1, 375.3, 382
See application file for complete search history.

(56) References Cited

U.S. PATENT DOCUMENTS

| | | | | |
|---|---|---|---|---|
| 1,685,585 | A * | 9/1928 | Grimes ............... 242/375.1 |
| 3,384,321 | A * | 5/1968 | Becker et al. ........ 242/375.1 |
| 4,003,552 | A * | 1/1977 | Sobolewski ............ 254/283 |
| 6,042,087 | A * | 3/2000 | Heinemann ............ 254/364 |
| 6,065,705 | A | 5/2000 | Schmitt |
| 6,991,064 | B2 * | 1/2006 | Ehrenleitner ............ 182/141 |
| 7,025,334 | B2 * | 4/2006 | Ehrenleitner ............ 254/278 |
| 7,150,424 | B2 * | 12/2006 | Hopper ............... 242/375.1 |
| 7,168,686 | B2 * | 1/2007 | Ehrenleitner ........... 254/371 |

* cited by examiner

*Primary Examiner*—Emmanuel M Marcelo
(74) *Attorney, Agent, or Firm*—Schiff Hardin LLP (57) ABSTRACT

A height-adjustably mounted apparatus has a flexible supply line that is conducted to the apparatus from above and is provided with a weight compensation device so that the apparatus can be easily adjusted to different vertical positions. The weight compensation device includes a cable drum that accepts a first carrying cable which is loaded with the height-adjustably mounted apparatus and is subjected to a force directed opposite to the weight of the device and the weight compensation device includes a second carrying cable that is accepted on the cable drum and has an end secured to a supply line at a fastening location, so that the fastening location is lifted by the second carrying cable during vertical adjustment of the apparatus.

15 Claims, 6 Drawing Sheets

WEIGHT COMPENSATION DEVICE

BACKGROUND OF THE INVENTION

The present invention is directed to a weight compensation device or counterbalance device for a height-adjustable apparatus or device that is connected to a flexible supply line conducted to the mounted device from above. The compensation or counterbalancing device comprises a cable drum that accepts a first carrying cable loaded with the height-adjustable device and that is loaded by a force directed opposite to the weight of the height-adjustable mounted device.

Weight compensation devices or counterbalance devices are utilized in many height-adjustable devices or apparatuses so that the height-adjustable device can be effortlessly and exactly positioned in height without exerting increased force to overcome the force of gravity and will remain in this position that has been set. A typical area of employment for such weight compensation devices occurs in the field of medical-technical devices, such as x-radiators, etc., which are often secured in the x-ray room via a ceiling mount and that must be freely positionable in all three spatial directions with the assistance of the ceiling mount and must additionally be pivotable around a vertical and/or horizontal swiveling axis.

U.S. Pat. No. 6,065,705, whose disclosure is incorporated herein by reference thereto and which claims priority from German 197 47 393, shows an example of such an x-radiator suspended in a ceiling mount. The ceiling mount is composed of what is referred to as a telescope carriage that is displaceable along a bridge mounted underneath the ceiling of the x-ray room. In order to achieve the two-dimensional adjustment, the bridge is seated at corresponding suspensions in the room movable transversely to the motion direction of the telescope carriage. At its underside, the telescope carriage comprises a telescoping column at whose lower end the x-radiator is, in turn, suspended. Pivotable around the telescoping column, the x-radiator is secured to the telescoping column by means of a support mount. The telescope carriage includes a weight compensation device, wherein the cable drum is situated inside the telescope carriage and a carrying cable proceeds downward through the telescoping column proceeding from the cable drum. The cable drum is loaded by a coil spring arranged inside the cable drum that will exert a force on the cable drum that opposes the weight of the x-radiator device and mount.

The x-radiator is also connected via various lines in a standard way to other devices belonging to the x-ray apparatus. For example, an x-ray generator supplies the x-radiator with a high voltage via a high-voltage line. Over and above this, the x-radiator is connected, for example, to control signal or data lines by which data and control signals can be exchanged between other components of the x-ray apparatus and the x-radiator. These various lines are combined inside a hose, for example a ribbed or corrugated hose, that is conducted upward from the terminal location of the x-radiator to the telescoping carriage and proceeds from the latter via the bridge to a terminal location in the room or, respectively, to the other devices. Such lines shall be referred to as supply lines hereinafter, regardless of whether they are a matter of a hose with a plurality of separate lines located therein, of electrical lines or, for example, of compressed air, gas, water and/or hydraulic lines, and regardless of the exact function of these lines.

One problem with such a height-adjustable device with supply lines brought in from above is that the supply lines must be dimensioned with respect to their length so that the maximum lowering in a vertical direction is not negatively affected. This, in turn, has the disadvantage that the supply lines are too long in and of themselves when the device is in the upper position and hang into the working area and, thus, limit the user-friendliness of the device, especially given a very high working position of the device, for example, given only a very slight extension of the telescoping column of the ceiling mount. In the extreme case, swiveling around the vertical axis can even be greatly impeded by the dangling supply line. This problem is necessarily all the more pronounced the greater the height adjustment range of the device.

SUMMARY OF THE INVENTION

It is, therefore, an object of the present invention to create a weight compensation device with the improvement of being user-friendly. This object is achieved by a weight compensation device for a height-adjustable apparatus that is connected to a flexible supply line conducted to the apparatus from above. The compensation device comprises a cable drum that accepts a first carrying cable loaded with the height-adjustable apparatus and that is loaded by a force directed opposite to the weight of the apparatus. The improvements are a second carrying cable accepted by the cable drum that is secured to the supply line so that, given an upward adjustment of the apparatus, the fastening location of the supply line is automatically pulled upward as well as the second carrying cable.

Inventively, the weight compensation device comprises a second carrying cable accepted by the cable drum that is secured to the supply line in a region at a distance from the terminal location of the supply line at the height-adjustable apparatus. Thus, given an upward adjustment of the apparatus, the supply line is automatically pulled upward as well by the second carrying cable in the region around the fastening location of the second carrying cable. By employing the additional cable, which has one end accepted on the cable drum that is already present for the first carrying cable, the supply lines can be automatically pulled upward out of the work area matched to the respective height adjustment of the apparatus, as a result whereof the accessibility to the field of operation of the apparatus is improved and, thus, the operation thereof is simplified and more pleasant. In particular, an unimpeded pivotability of the apparatus around the vertical axis, for example around the telescoping column, is assured, even in an extremely high position for the height-adjusted apparatus.

The invention is therefore especially suited for devices with ceiling mounts, as initially set forth. Over and above this, the invention can also be employed in all other height-adjustable apparatuses wherein corresponding supply lines are conducted up and that comprise a suitable weight compensation or counterbalancing device.

Steel cables are preferably employed as the carrying cable. Alternatively, however, arbitrary other cables or even chains, belts or the like having adequate carrying power and resistance to tearing or breaking can be employed as the first and/or second carrying cable. Below, the term "carrying cable", therefore, also explicitly covers chains, belts and the like.

In order to generate an adequate force on the cable drum that counters the weight of the apparatus, for example a spring integrated in the cable drum, particularly a coil spring or motive spring, as shown in the above-mentioned U.S. Pat. No. 6,065,705, has been proposed. A structure composed of a plurality of individual springs like these can be employed. Alternatively, other methods can also be employed for the weight compensation, for example a coupling of the cable drum to corresponding counterweights. The employment of coiled springs or motive springs, however, has the advantage that these designs are extremely compact and, thus, space-saving.

In a first version, the weight compensation device is built so that the second carrying cable is taken up or, respectively, unwound by the same length when the first carrying cable is taken up or unwound from the cable drum by a certain length. For example, the vertical path of the second carrying cable to which the supply line is secured exactly corresponds to the vertical path of the first carrying cable to which the adjustably mounted apparatus is secured. Thus, the distance between the region of the supply line to which the second carrying cable is secured and the apparatus itself will always remain constant, even given a height adjustment.

This can be realized in a very simple way in that the first and second carrying cables proceed in a common channel in the cable drum or in two parallel channels that proceed on the same diameter.

Alternatively, the cable drum can also be composed of a plurality of separate, discrete rollers for the carrying cables that are coupled to one another via a suitable gearing having a 1:1 transmission.

In a second version, the weight compensation device is designed so that the second carrying cable is unwound or, respectively, taken up by a longer or shorter length when the first carrying cable is unwound from or taken up onto the cable drum by a certain length. For example, the path of the second carrying cable is lengthened or, respectively, shortened with respect to the first carrying cable holding the device itself.

This, for example, can likewise be achieved by separate rollers in the cable drum that are coupled via corresponding gearing with the suitable transmission ratio.

In an especially preferred exemplary embodiment, a different path length of the carrying cable is realized, however, in that the first and second carrying cables are accepted in separate channels that proceed on different diameters in the cable drum. This realization is especially simple and cost-beneficial, since corresponding channels merely have to be introduced into a single cable drum.

A design is thereby especially preferred wherein the second carrying cable transverses a shorter path than the first carrying cable, and this is capable of being realized in that the channel for the acceptance of the second carrying cable proceeds on a smaller diameter in the cable drum than the channel for the acceptance of the first carrying cable. In such a version, the second carrying cable can preferably be attached in a region of the supply line that comprises a relatively great distance from the terminal location of the operating lines on the height-adjustable apparatus, so that the supply line is just still suspended by the second carrying cable so that unimpeded operation is possible in the highest possible position. As a result of the different path lengths of the first and second carrying cables, the distance of the suspension point of the supply line at the second carrying cable displaces farther and farther upward away from the apparatus when the apparatus is lowered, as a result whereof more and more space is made available to the operator.

In an especially preferred exemplary embodiment, the weight compensation device comprises an arrester cable additionally guided on the cable drum that secures the apparatus given a breaking of the first carrying cable. For example, this arrester cable extends parallel to the first carrying cable and is dimensioned in terms of its lengths so that it is only loaded if the first carrying cable breaks. An arbitrary cable, a chain, a belt or the like with adequate carrying power and resistance to breaking or tearing can likewise be employed as the arrester cable.

If there is a great range of height adjustment with particularly long supply hoses, it is desirable that the weight compensation device includes a plurality of second carrying cables, for example two separate carrying cables, that are secured to the supply line in different locations in order to, thus, pull the supply line up at a plurality of locations in common with the apparatus. The second carrying cables can thereby be respectively mounted in the cable drum so that they traverse a precisely defined, suitable path length, so that the supply hose is optimally held in every height position. In addition, it is also possible that a carrying cable is secured to a supply line at a plurality of locations.

The employment of a plurality of second carrying cables is also handy when various separate supply lines proceed to the apparatus that, for example, cannot be guided in common within a single hose. These second carrying cables can then be respectively secured to the various supply lines and correspondingly pull these up out of the work area when the device is adjusted upward. However, it is also possible that a single second carrying cable is simultaneously secured to a plurality of separate supply lines and pulls these supply lines up in common.

Other advantages and features of the invention will be readily apparent from the following description, the claims and drawings.

DESCRIPTION OF THE PREFERRED EMBODIMENTS

Figure 1:
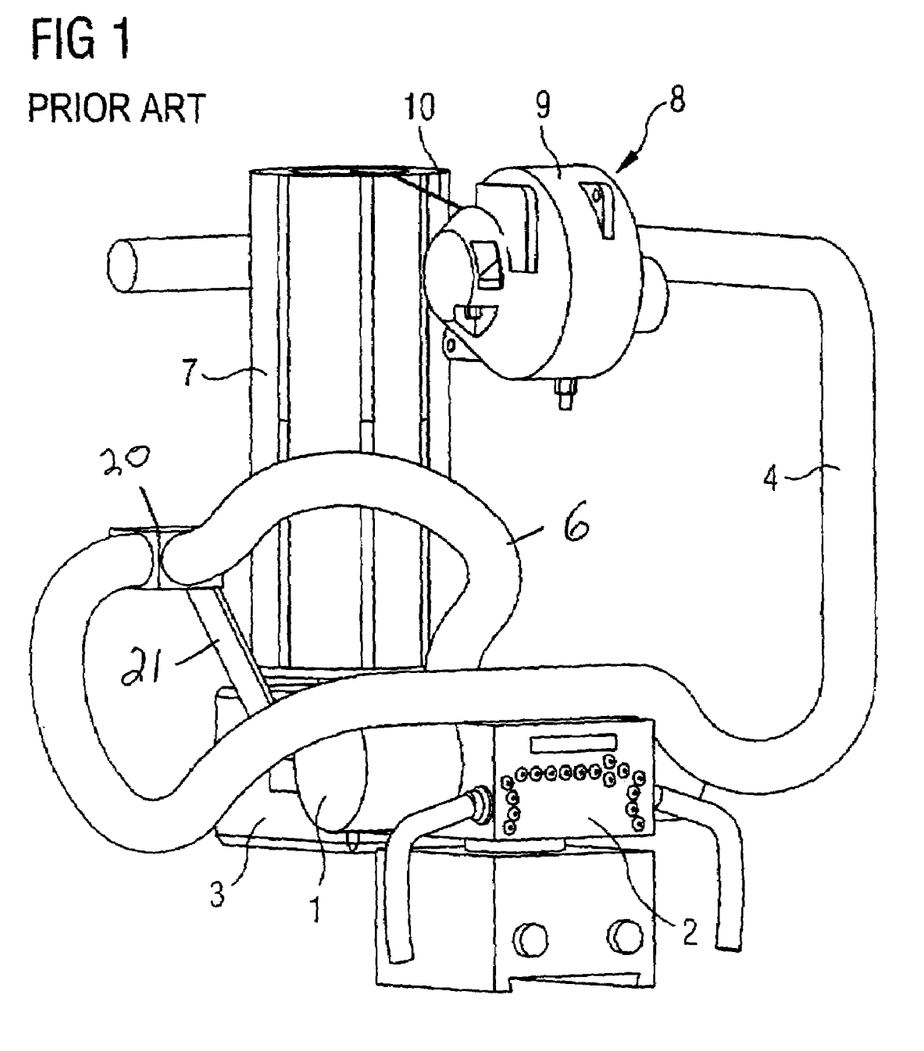
FIG. 1 is a perspective view of an x-radiator secured to a ceiling mount in a retracted position with a weight compensation device according to the prior art.
Figure 2:
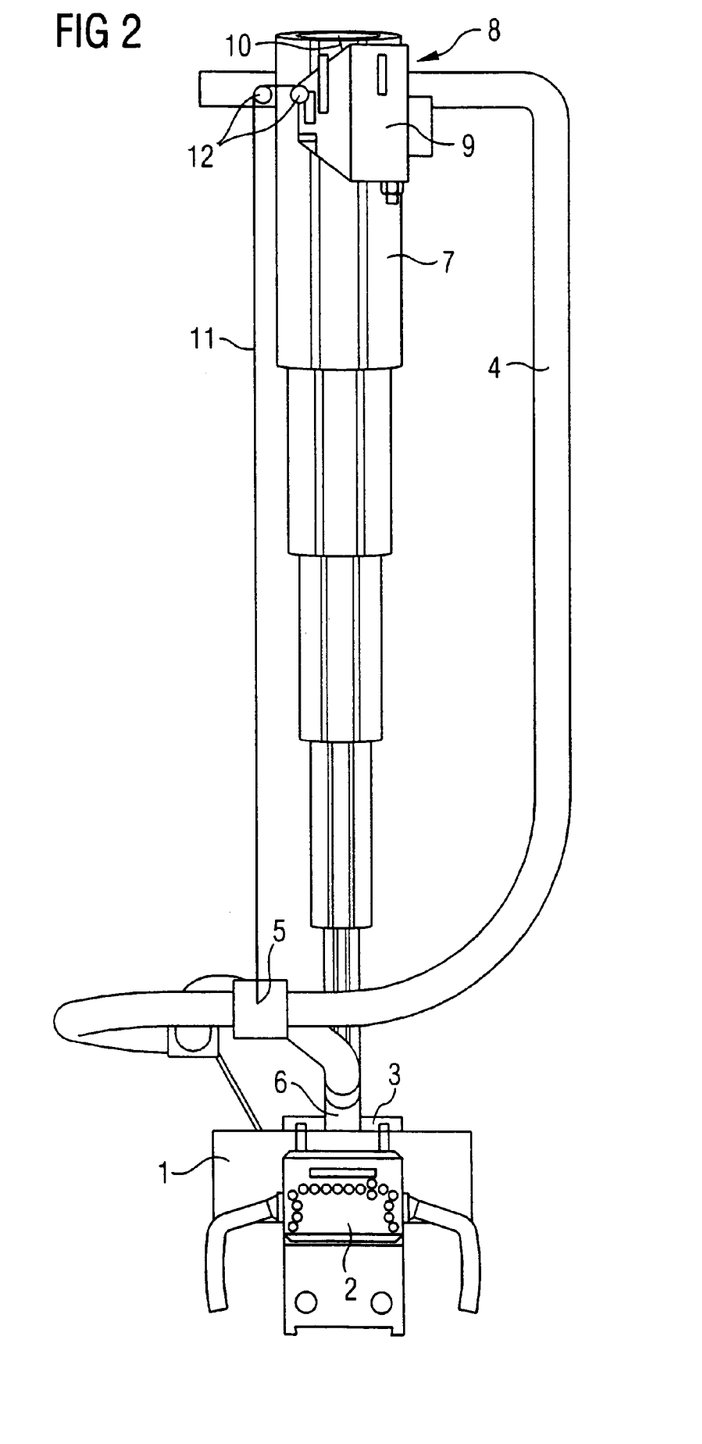
FIG. 2 is a front view of the device of FIG. 1 in an extended condition but with the inventive weight compensation device having a second carrying cable for the supply line.
Figure 3:
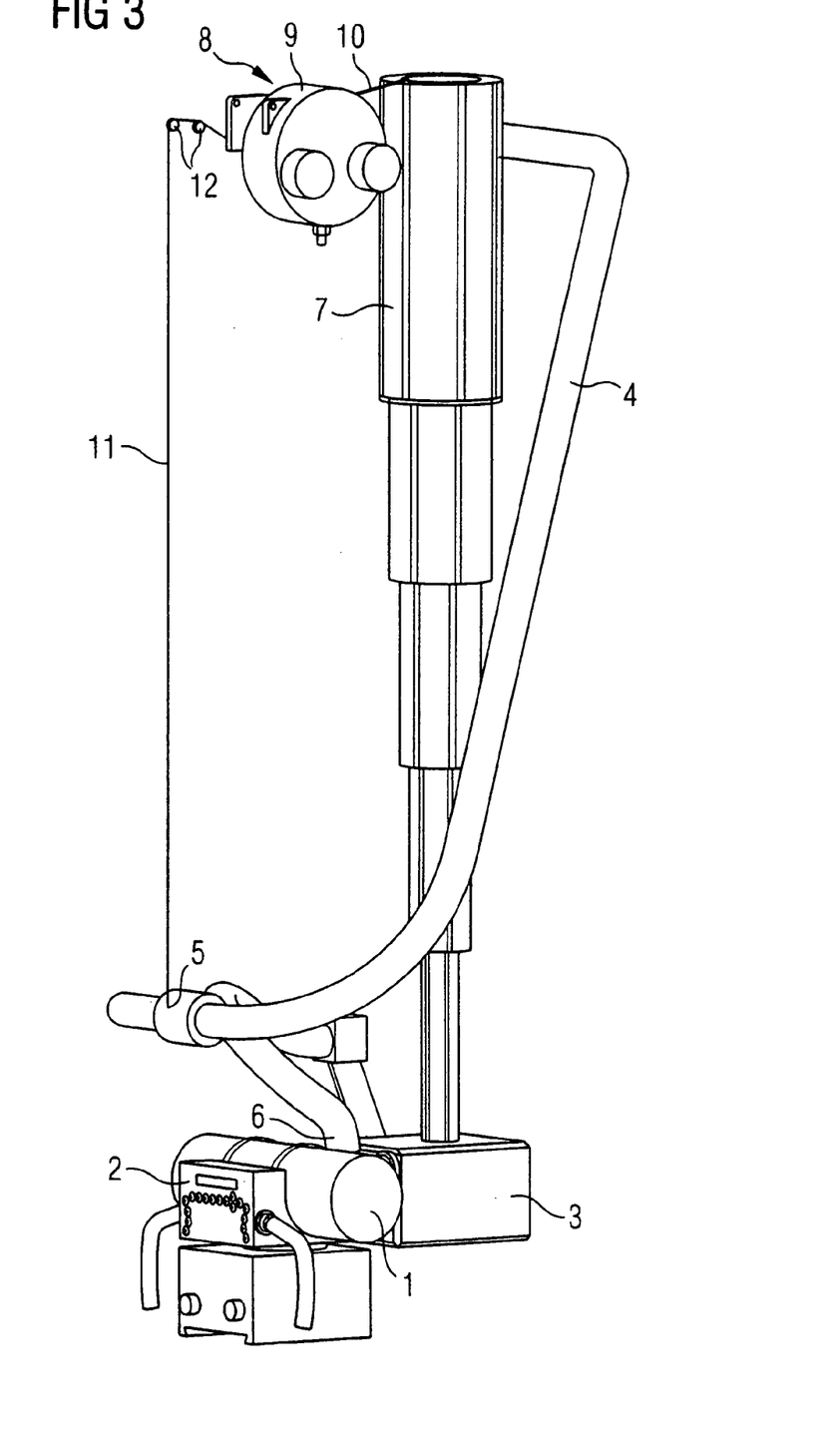
FIG. 3 is a perspective view of the device according to FIG. 2.

An x-radiator 1, which is secured to a ceiling mount which has a telescoping column 7 in a standard way is illustrated in FIG. 1. For weight compensation, the device is equipped with a traditional weight compensation device 8 known from the prior art. This is composed of a cable drum seated in a cable drum housing 9, which cable drum accepts a carrying cable 10 that is conducted downward through the tubular telescopic or telescoping column 7 from the cable drum and has its end connected to the x-radiator 1 or, respectively, a bracket or carriage 3 for the x-radiator 1 and, thus, the cable 10 supports the load of the x-radiator and the bracket.

The x-radiator 1 is supplied with the necessary high voltage and required data signals or, respectively, control signals, which may be sent back and forth between the x-radiator 1 and additional components of the x-ray device through a supply line 4, which may be a ribbed or corrugated hose. As illustrated, the supply line 4 extends to a junction 20, which is held by a bracket 21 above the carriage 3. A second supply line 6 extends from the junction 20 to the actual x-ray control panel 2 of the x-radiator 1. The supply line 4 is dimensioned with such a length that the device 1 can be moved into the lowest position, wherein the telescoping column 7 is entirely extended.

As illustrated in FIG. 1, the problem occurs when the x-radiator 1 is pushed up into its highest position. The supply line 4, which is too long for this position, rests on the x-radiator 1 or, respectively, the bracket 3 and thereby impedes the operation of the device. In particular, the x-radiator 1 can no longer be pivoted unimpeded around the longitudinal axis of the telescoping column 7. In the extreme case, the supply line 4 can also cover the control panel 2 of the x-radiator 1.

In order to largely avoid such limitations of the user-friendliness in an upper position of the x-radiator 1, a second carrying cable 11 (see FIGS. 2-5) is inventively employed and is accepted by the cable drum of the weight compensation device 8. It has an end that is secured to a fastening location 5 on the supply line 4 that is located a certain distance above the connection of the supply line 6 to the x-radiator 1. This second carrying cable sees to it that the supply line 4 is located above the x-radiator 1 in every position of the x-radiator 1.

Figure 4:
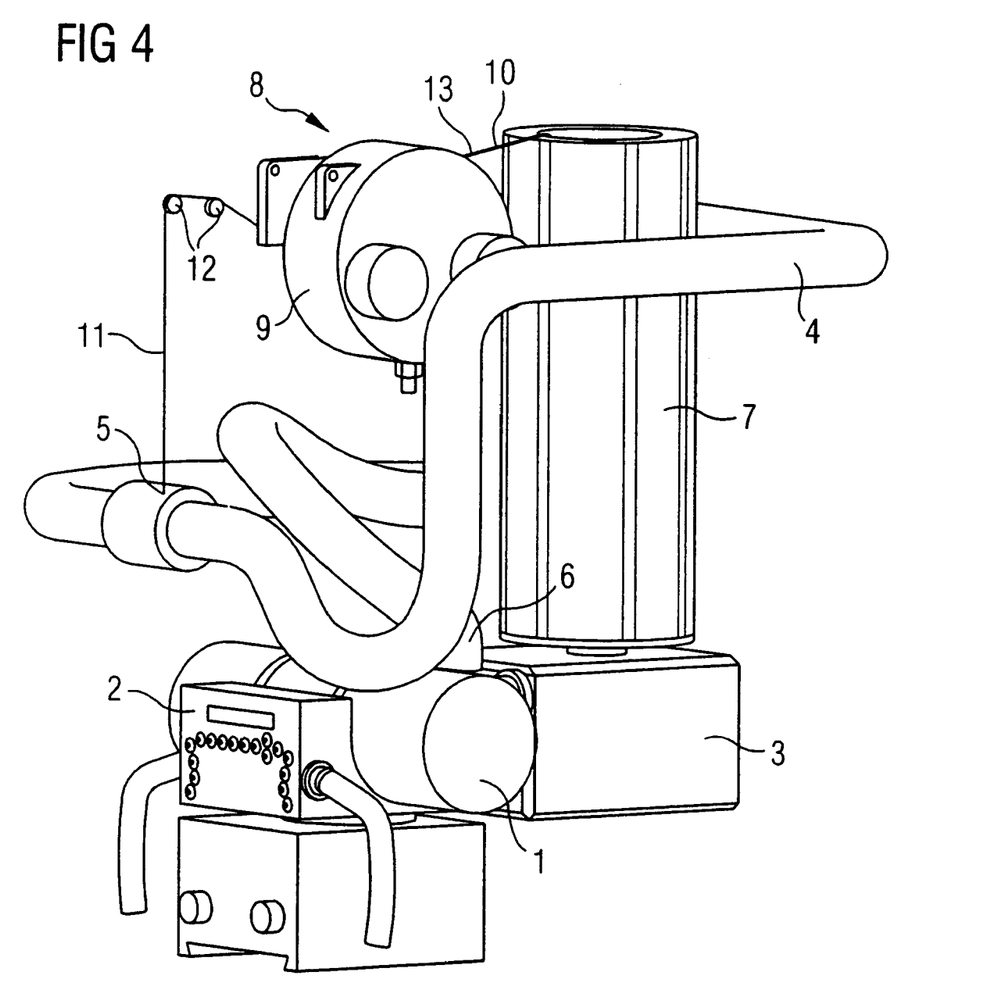
FIG. 4 is a perspective view of the device according to FIGS. 2 and 3 in a retracted condition, as seen from the front, right side.
Figure 5:
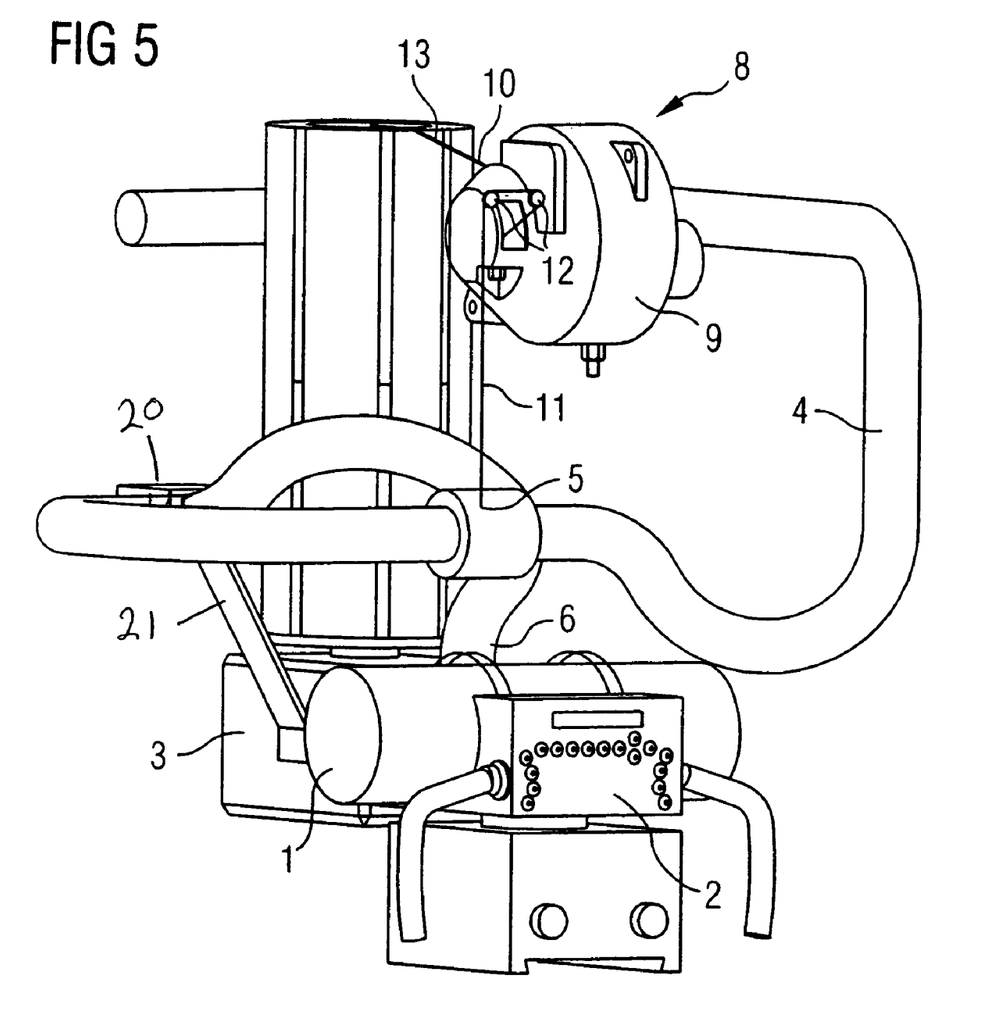
FIG. 5 is a perspective view of the device according to FIG. 4 in the same adjusted condition but from the left, front side.

A comparison of FIGS. 4 and 5 to FIG. 1 particularly shows how the supply line 4 is held above the x-radiator 1 with the second carrying cable 11 when the x-radiator is in the upper position, i.e., when the telescoping column 7 is retracted, so that the x-radiator 1 is freely pivotable and the control panel of the x-radiator 1 is freely accessible. The second carrying cable 11 can thereby be conducted out from the cable drum housing 9 at an arbitrary location and can be guided as wanted via deflection rollers 12, so that the carrying cable can pull the fastening location 5 and the supply line 4 up unimpeded.

Figure 6:
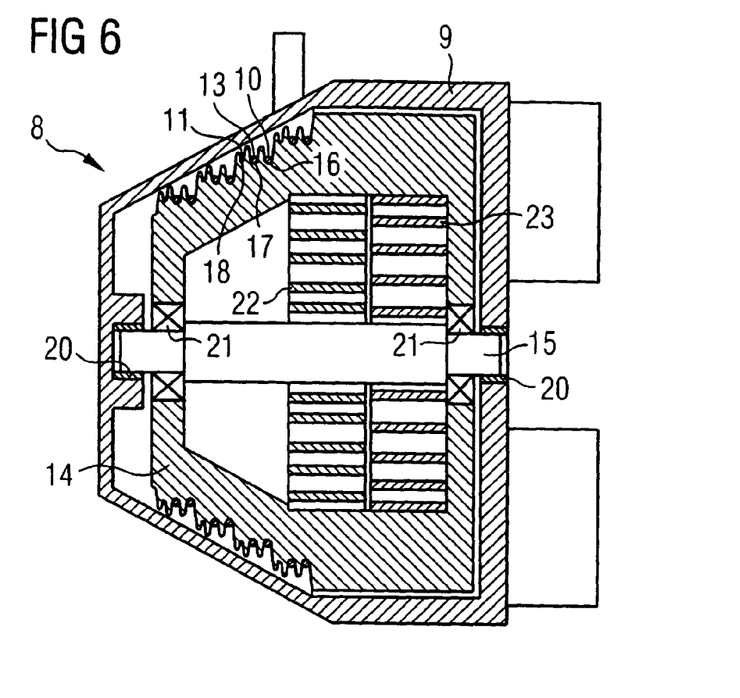
FIG. 6 is a schematic cross-sectional view of a cable drum of the inventive weight compensation device in a first exemplary embodiment.
Figure 7:
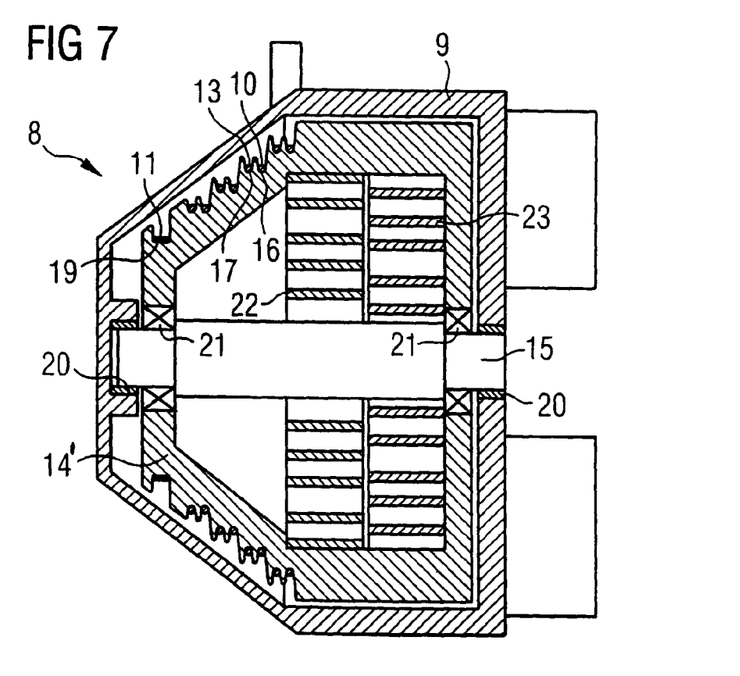
FIG. 7 is a schematic cross-sectional view of a cable drum of the inventive weight compensation device in a second exemplary embodiment

FIGS. 6 and 7 show two different versions for fashioning the cable drum 14 and 14' of the weight compensation device. Both cable drums 14 and 14' are a respective matter of conically tapering cable drums in which various channels, such as 16, 17, 18 and 19 are introduced for carrying cables and arrester cables 10, 11 and 13.

In detail, three cables 10, 11 and 13 run in both cable drums 14 and 14', whereby one cable 10 is the first carrying cable and a cable 13 running parallel is the arrester cable that holds the x-radiator 1 when the carrying cable 10 breaks and prevents an uncontrolled pancaking of the x-radiator 1. The inventive second carrying cable 11 is guided in either the channel 18, as illustrated in FIG. 6, or the channel 19, as illustrated in FIG. 7.

In both exemplary embodiments, the cable drums 14 and 14' are rotatably mounted on a shaft 15 via two bearings 21. The shaft 15 is torsionally held in bearings 20 within the cable drum housing 9 at its respective ends. The force opposing the weight of the x-radiator 1 and the bracket 3 is exerted via coil springs 22 and 23 that have a radially inward end secured to the torsional shaft 15 and their other end, which is a radially outwardly disposed end secured to the cable drum 14. These springs provide a force which counterbalances and oppose the weight of the x-radiator 1 and the associated carriage 3. The force via the springs 22 and 23 is set so that the x-radiator 1 can be effortlessly moved into any arbitrary height position nearly without exertion of force and remains at that position. The user of two parallel coils springs 22 and 23 has the advantage that, if one spring here breaks, the device is at least still held by a second spring, although it is with half the force.

In the first exemplary embodiment of FIG. 6, the channel 18 for the second carrying cable 11 proceeds exactly parallel to the channels 16 and 17 for the first carrying cable 10 and the arrester cable 13, so that the peripheral length of the paths on the cable drum are the same. The second carrying cable 11 for the supply line, therefore, always traverses exactly the same distance as the carrying cable 10 and the parallel arrester cable 13. Regardless of the height setting, the distance between a fastening point 5 of the supply line 4 to which the second carrying cable 11 is secured and the x-radiator 1 itself will remain the same. This is shown in FIGS. 2-5.

In the second exemplary embodiment according to FIG. 7, the second carrying cable 11 for the supply line 4 lies in a channel 19 that is arranged close to the end of the conical cable drum 14' and has a smaller circumference, so that the peripheral path of the channel 19 is less than the paths for the channels 16 and 17. For example, this channel 19 proceeds on a smaller circumference than the channels 16 and 17 for the first carrying cable 10 and the arrester cable 13, which proceed parallel in the exemplary embodiment according to FIG. 6. As a result thereof, the second carrying cable 11 for the supply line 4 will traverse only a shorter distance given an adjustment of the x-radiator 1 by a certain path length.

In the second exemplary embodiment, the length of the second carrying cable 11 for the supply line 4 is selected so that the same relationships as shown for the first exemplary embodiment in FIGS. 4 and 5 are present in the retracted position, i.e., in its highest position of the x-radiator 1. The supply hose is therefore located above the x-radiator 1 just barely sufficing for an unimpeded operation of the x-radiator 1. When, however, the x-radiator 1 is pulled farther down into its second version and the telescoping column 7 is extended, then the region of the supply line 4 to which the end of the second carrying cable 11 is secured traverses less of a distance than the x-radiator 1 itself. As a result thereof, the distance between the x-radiator 1 and the fastening location 5 of the second carrying cable increases, so that the operator's freedom of movement becomes greater and greater. This results therein that the operator is usually provided with more space, except in the highest position for the x-radiator 1, than in the arrangement of FIG. 6 with the second carrying cable 11 and the first carrying cable 10 extending on parallel paths on the drum 14.

The Figures show how, given an upward adjustment of the x-radiator 1, the supply line 4 is also pulled up away from the work area and, thus, the user-friendliness is considerably improved. Such an inventive device is therefore particularly advantageous when it is operated in a room having a relatively low ceiling height, so that, for example, a ceiling mount is very frequently operated in a retracted condition or position. Since the path of the second carrying cable 11 needed for moving the supply line 4 is realized via the spring traction that is already present and, moreover, needed for the compensation of the weight of the x-radiator 1, a very cost-beneficial application of the invention is also possible.

Although various minor modifications may be suggested by those versed in the art, it should be understood that we wish to embody within the scope of the patent granted hereon all such modifications as reasonably and properly come within the scope of our contribution to the art.

We claim:

1. A weight compensation device for a height-adjustable apparatus that is connected to a flexible supply line conducted to the apparatus from above, the compensation device comprising a cable drum that accepts a first carrying cable loaded with the height-adjustable apparatus and means for providing a force directed opposite to the weight of the apparatus, the improvements comprising a second carrying cable being accepted by the cable drum and being secured to the supply line so that, given an upward adjustment of the device, the supply line is automatically pulled upward as well by the second carrying cable in a region around the fastening location of the second carrying cable to the supply line.

2. A weight compensation device according to claim 1, wherein the cable drum has the same peripheral length for the paths of, the first carrying cable and the second carrying cable, so that with a rotation of the drum, the same length of cable is unwound or taken up.

3. A weight compensation device according to claim 2, wherein the first and second carrying cables are accepted on a cable drum in a common channel.

4. A weight compensation device according to claim 2, wherein the cable drum has two channels proceeding parallel to each other with the same diameter for receiving the first and second carrying cables.

5. A weight compensation device according to claim 1, wherein the peripheral length of the path for the second carrying cable on the cable drum is different than the peripheral length of the path for the first carrying cable.

6. A weight compensation device according to claim 5, wherein the first and second carrying cables are accepted in channels having different diameters on the cable drum.

7. A weight compensation device according to claim 6, wherein the channel for acceptance of the second carrying cable proceeds on a smaller diameter in the cable drum than the channel for accepting the first carrying cable.

8. A weight compensation device according to claim 1, in which an additional arrester cable is guided in the carrier drum and secures the device given a breaking of the first carrying cable.

9. A weight compensation device according to claim 1, which includes a plurality of second carrying cables being secured in different regions to the supply line.

10. A weight compensation device according to claim 1, wherein the height-adjustable apparatus has a plurality of separate supply lines, and said compensation device has a second carrying cable for each of the separate supply lines.

11. A weight compensation device according to claim 1, wherein the means providing a force directed opposite the weight of the apparatus comprises a spring mechanism positioned in the cable drum.

12. A weight compensation device according to claim 1, wherein the means for creating a force acting opposite the weight of the apparatus includes a pair of spring mechanisms for generating the force disposed in the cable drum.

13. An apparatus being adjustably mounted on a column, said apparatus having flexible supply lines extending from above to the apparatus, a weight compensation device including a cable drum having a first carrying cable loaded with the apparatus, means for loading a force directed opposite to the weight of the apparatus, and a second carrying cable accepted by the cable drum and being secured to a fastening location on the supply line, so that with upward adjustment of the apparatus, the supply line is automatically pulled upward in the region of the fastening location.

14. An apparatus according to claim 13, wherein the path on the cable drum for both the first carrying cable and the second carrying cable have an equal length, so that, during adjustment of the apparatus, a distance between the fastening location and the adjustable apparatus remains constant.

15. An apparatus according to claim 13, wherein the annular length of the path for the first carrying cable is greater than the annular length of the path for the second carrying cable so that a distance between the fastening location and the mounted apparatus increases as the position of the apparatus is raised.

* * * * *